United States Patent [19]

Stähle et al.

[11] 4,025,607
[45] May 24, 1977

[54] PROPARGYL-SUBSTITUTED 2-PHENYLAMINO-2-IMIDAZOLINES AND SALTS THEREOF

[75] Inventors: Helmut Stähle; Herbert Köppe; Werner Kummer, all of Ingelheim am Rhein; Klaus Stockhaus, Bingen (Rhine); Wolfgang Hoefke, Budenheim; Franz Josef Kuhn, Bingen (Rhine), all of Germany

[73] Assignee: Boehringer Ingelheim GmbH, Ingelheim am Rhein, Germany

[22] Filed: May 17, 1976

[21] Appl. No.: 687,250

[30] Foreign Application Priority Data

May 24, 1975 Germany .......................... 2523103

[52] U.S. Cl. .......................... 424/273; 260/309.6; 260/309.7
[51] Int. Cl.² ....................... C07D 233/50
[58] Field of Search .............. 260/309.6, 309.7; 424/273

[56] References Cited

UNITED STATES PATENTS

| | | | |
|---|---|---|---|
| 3,804,833 | 4/1974 | Stähle et al. | 260/309.6 |
| 3,807,485 | 1/1973 | Stähle et al. | 260/309.6 |
| 3,850,926 | 11/1974 | Stähle et al. | 260/309.6 |

*Primary Examiner*—Natalie Trousof
*Attorney, Agent, or Firm*—Hammond & Littell

[57] ABSTRACT

Compounds of the formula

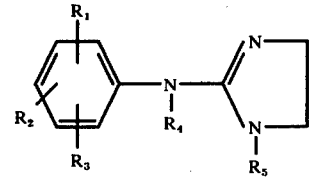

wherein
$R_1$, $R_2$ and $R_3$, which may be identical to or different from each other, are each hydrogen, fluorine, chlorine, bromine, methyl, ethyl, methoxy or trifluoromethyl, and
$R_4$ and $R_5$ are each hydrogen or propargyl, but other than both hydrogen or both propargyl at the same time, and non-toxic, pharmacologically acceptable acid addition salts thereof; the compounds as well as the salts are useful as analgesics and hypotensives.

8 Claims, No Drawings

PROPARGYL-SUBSTITUTED 2-PHENYLAMINO-2-IMIDAZOLINES AND SALTS THEREOF

This invention relates to novel propargyl-substituted 2-anilino-2-imidazolines and non-toxic acid addition salts thereof, as well as to methods of preparing these compounds.

More particularly, the present invention relates to a novel class of 2-anilino-2-imidazolines represented by the formula

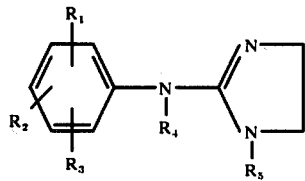

(I)

wherein $R_1$, $R_2$ and $R_3$, which may be identical to or different from each other, are each hydrogen, fluorine, chlorine, bromine, methyl, ethyl, or methoxy or trifluoromethyl when sterically possible, and $R_4$ and $R_5$ are each hydrogen or propargyl, but other than both hydrogen or both propargyl at the same time, and non-toxic, pharmacologically acceptable acid addition salts thereof.

Within this class of compounds are those compounds where $R_1$, $R_2$ and $R_3$ are each hydrogen, fluorine, chlorine, bromine, methyl, ethyl, methoxy or trifluoromethyl, $R_4$ is propargyl, and $R_5$ is hydrogen or those compounds where $R_1$, $R_2$ and $R_3$ are each hydrogen, fluorine, chlorine, bromine, methyl, ethyl, methoxy, or trifluoromethyl, $R_4$ is hydrogen, and $R_5$ is propargyl.

The compounds embraced by formula I above may be prepared by the following methods:

Method A

By reacting a 2-anilino-2-imidazoline of the formula

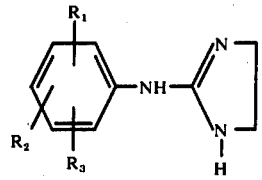

(II)

wherein $R_1$, $R_2$ and $R_3$ have the same meanings as in formula I, with a propargyl halide of the formula

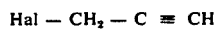

Hal — CH₂ — C ≡ CH    (III)

wherein Hal is halogen, preferably bromine.

This alkylation reaction is performed by heating the reactants, preferably in the presence of a polar or a non-polar organic solvent, to a temperature between about 50° and 150° C. The specific reaction conditions depend largely upon the reactivity of the reactants. It is advantageous to provide an excess of the propargyl halide over and above the stoichiometrically required amount and to perform the alkylation reaction in the presence of an acid-binding agent, such as sodium carbonate. The reaction exclusively yields compounds of the formula I wherein $R_4$ is propargyl and $R_5$ is hydrogen.

Method B

By reacting a metal salt of a 2-anilino-2-imidazoline of the formula

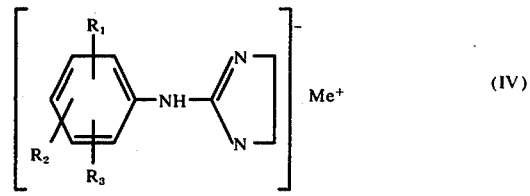

(IV)

wherein $R_1$, $R_2$ and $R_3$ have the same meanings as in formula I, and

Me$^+$ is a metal cation, preferably an alkali metal cation, especially Na$^+$, with a propargyl halide of the formula III.

This reaction is most advantageously carried out in a non-polar solvent, such as tetrahydrofuran, at elevated temperatures up to 150° C; the reaction goes to completion usually after 1 to 2 hours.

This method yields mainly compounds of the formula I wherein $R_5$ is propargyl and $R_4$ is hydrogen, although minor amounts of the corresponding isomeric compounds, i.e., those where $R_4$ is propargyl and $R_5$ is hydrogen, may concurrently be formed. The isomers can be readily separated from each other by conventional methods.

The desired position of the propargyl substitution can thus be selectively controlled by choice of the method of synthesis; the position of propargyl substitution in the end product can be determined by NMR-spectrascopy [cf. H. Stähle et al., Liebigs Ann. Chem. 751, 159 et.seq. (1971)].

The starting compounds of the formula II are known compounds; they are, for example, disclosed in Belgian Pat. Nos. 623,305; 687,656; 687,657; and 705,944.

The starting compounds of the formula IV may be obtained by reacting a compound of the formula II with a metal hydride or metalalkyl under absolute conditions.

The compounds embraced by formula I are organic bases and therefore form acid addition salts with inorganic and organic acids. Examples of non-toxic, pharmacologically acceptable acid addition salts are those formed with hydrochloric acid, hydrobromic acid, sulfuric acid, phosphoric acid, nitric acid, acetic acid, propionic acid, butyric acid, caproic acid, valeric acid, oxalic acid, malic acid, tartaric acid, citric acid malonic acid, benzoic acid, cinnamic acid, ascorbic acid, methanesulfonic acid, 8-chlorotheophylline or the like.

The following examples illustrate the present invention and will enable others skilled in the art to understand it more completely. It should be understood, however, that the invention is not limited solely to the particular examples given below.

EXAMPLE 1

2-[N-Propargyl-N-(2',6'-dichloro-phenyl)-amino]-2-imidazoline by method A

A mixture consisting of 6.9 gm (0.03 mol) of 2-[N-(2',6'-dichloro-phenyl)-amino]-2-imidazoline, 2.5 ml of (110% of stoichiometrically required amount) of propargyl bromide, 3.5 gm of sodium carbonate, and 25 ml of absolute methanol was refluxed for three hours, while stirring. Thereafter, the reaction mixture was evaporated to dryness, and the residue was dissolved in dilute hydrochloric acid. The resulting acidic solution was extracted several times with ether, the ethereal extracts being discarded. The aqueous acidic phase was now stepwise adjusted to gradually increasing pH-values with dilute sodium hydroxide and fractionally extracted with ether after each adjustment step. The thin-layer chromatographically pure ether extracts were combined, dried over anhydrous calcium sulfate, and evaporated to dryness. The residue was stirred with about 25 ml of ether, and the white crystallizate formed thereby was suction-filtered off and washed with a little ether. 2.8 gm (34.8% of theory) of the compound of the formula

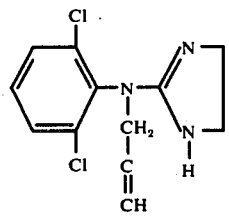

having a melting point of 116.5° – 118.5° C were obtained. The product was insoluble in water, but readily soluble in polar organic solvents, such as methanol or ethanol.

EXAMPLE 2

2-[N-Propargyl-N-(2',3'-dichloro-phenyl)-amino]-2-imidazoline by method A

A mixture consisting of 6.9 gm (0.03 mol) of 2-[N-(2',3'-dichloro-phenyl)-amino]-2-imidazoline, 2.5 ml (110% of the stoichiometrically required amount) of propargyl bromide, 3.5 gm of sodium carbonate and 25 ml of tetrahydrofuran was refluxed for three hours, while stirring. Thereafter, the reaction solution was allowed to cool, and the precipitate formed thereby was suction-filtered off and dissolved in dilute hydrochloric acid. The resulting acidic solution was extracted several times with ether (the ethereal extracts were discarded) and was then made alkaline with dilute sodium hydroxide, whereupon an oil separated out which crystallized throughout upon standing for a while. The crystallizate was suction-filtered off and washed with a little ether, yielding 2.3 gm (29.2% of theory) of thin-layer chromatographically pure 2-[N-propargyl-N-(2',3'-dichloro-phenyl)-amino]-2-imidazoline, m.p. 85.5°–87.5° C. The product was soluble in ethanol and dimethylsulfoxide, as well as in most other organic solvents, but insoluble in water; it dissolved in dilute hydrochloric acid to form its hydrochloride.

EXAMPLE 3

Using a procedure analogous to that described in Example 1, 29.5% of theory of 2-[N-propargyl-N-(2',6'-dibromo-phenyl)-amino]-2-imidazoline, m.p. 134°–135° C, was obtained from 2-[N-(2',6'-dibromo-phenyl)-amino]-2-imidazoline and propargyl bromide.

EXAMPLE 4

Using a procedure analogous to that described in Example 1, 48.0% of theory of 2-[N-propargyl-N-(2'-methyl-5'-fluoro-phenyl)-amino]-2-imidazoline was obtained from 2-[N-(2'-methyl-5'-fluoro-phenyl)-amino]-2-imidazoline and propargyl bromide. Its hydrobromide has a melting point of 207°–208° C.

EXAMPLE 5

Using a procedure analogous to that described in Example 1, 20.3% of theory of 2-[N-propargyl-N-(2'-trifluoromethyl-phenyl)-amino]-2-imidazoline, m.p. 107°–109° C, was obtained from 2-[N-(2'-trifluoromethyl-phenyl)-amino]-2-imidazoline and propargyl bromide.

EXAMPLE 6

Using a procedure analogous to that described in Example 1, 15.9% of theory of 2-[N-propargyl-N-(2',6'-dichloro-4'-bromo-phenyl)-amino]-2-imidazoline, m.p. 143°–144° C, was obtained from 2-[N-(2',6'-dichloro-4'-bromo-phenyl)-amino]-2-imidazoline and propargyl bromide.

EXAMPLE 7

Using a procedure analogous to that described in Example 2, 51.2% of theory of 2-[N-propargyl-N-(2'-chloro-3'-methyl-phenyl)-amino]-2-imidazoline, m.p. 92°–93° C, was obtained from 2-[N-(2'-chloro-3'-methyl-phenyl)-amino]-2-imidazoline and propargyl bromide.

EXAMPLE 8

Using a procedure analogous to that described in Example 1, 26.2% of theory of 2-[N-propargyl-N-(2',6'-diethyl-phenyl)-amino]-2-imidazoline, m.p. 69°–71° C, was obtained from 2-[N-(2',6'-diethyl-phenyl)-amino]-2-imidazoline and propargyl bromide.

EXAMPLE 9

Using a procedure analogous to that described in Example 1, 47.4% of theory of 2-[N-propargyl-N-(3'-methoxyphenyl)-amino]-2-imidazoline, m.p. 76°–77° C, was obtained from 2-[N-(3'-methoxy-phenyl)-amino]-2-imidazoline and propargyl bromide.

EXAMPLE 10

Using a procedure analogous to that described in Example 1, 48.5% of theory of 2-[N-propargyl-N-(2'-chloro-4'-methyl-phenyl)-amino]-2-imidazoline, m.p. 130°–131° C, was obtained from 2-[N-(2'-chloro-4'-methyl-phenyl)-amino]-2-imidazoline and propargyl bromide.

EXAMPLE 11

Using a procedure analogous to that described in Example 1, 65.5% of theory of 2-[N-propargyl-N-(2'-chloro-6'-methyl-phenyl)-amino]-2-imidazoline, m.p. 91°–93° C, was obtained from 2-[N-(2'-chloro-6'- methyl-phenyl)-amino]-2-imidazoline and propargyl bromide.

EXAMPLE 12

Using a procedure analogous to that described in Example 1, 28.6% of theory of 2-[N-propargyl-N-(2',5'-dichloro-phenyl)-amino]-2-imidazoline, m.p. 107°–109° C, was obtained from 2-[N-(2',5'-dichloro-phenyl)-amino]-2-imidazoline and propargyl bromide.

EXAMPLE 13

Using a procedure analogous to that described in Example 1, 56.0% of theory of 2-[N-propargyl-N-(2',4'-dichloro-phenyl)-amino]-2-imidazoline, m.p. 128°–129° C, was obtained from 2-[N-(2',4'-dichloro-phenyl)-amino]-2-imidazoline and propargyl bromide.

EXAMPLE 14

Using a procedure analogous to that described in Example 1, 55.7% of theory of 2-[N-propargyl-N-(2'-methyl-4'-chloro-phenyl)-amino]-2-imidazoline, m.p. 123°–125° C, was obtained from 2-[N-(2'-methyl-4'-chloro-phenyl)-amino]-2-imidazoline and propargyl bromide.

EXAMPLE 15

Using a procedure analogous to that described in Example 1, 62.2% of theory of 2-[N-propargyl-N-(2'-methyl-5'-chloro-phenyl)-amino]-2-imidazoline, m.p. 99°–101° C, was obtained from 2-[N-(2'-methyl-5'-chloro-phenyl)-amino]-2-imidazoline and propargyl bromide.

EXAMPLE 16

Using a procedure analogous to that described in Example 1, 26.4% of theory of 2-[N-propargyl-N-(2',6'-dimethyl-phenyl)-amino]-2-imidazoline, m.p. 116°–118° C, was obtained from 2-[N-(2',6'-dimethyl-phenyl)-amino]-2-imidazoline and propargyl bromide.

EXAMPLE 17

Using a procedure analogous to that described in Example 1, 80.0% of theory of 2-[N-propargyl-N-(2'-methyl-6'-ethyl-phenyl)-amino]-2-imidazoline, an oil, was obtained from 2-[N-(2'-methyl-6'-ethyl-phenyl)-amino]-2-imidazoline and propargyl bromide.

EXAMPLE 18

Using a procedure analogous to that described in Example 1, 59.6% of theory of 2-[N-propargyl-N-(3'-chlorophenyl)-amino]-2-imidazoline, m.p. 68°–69° C, was obtained from 2-[N-(3'-chloro-phenyl)-amino]-2-imidazoline and propargyl bromide.

EXAMPLE 19

1-Propargyl-2-[N-(2',6'-dichloro-phenyl)-amino]-2-imidazoline by method B 1.3 gm (0.03 mol) of an about 55% sodium hydride dispersion were added to a solution of 6.9 gm (0.03 mol) of 2-[N-(2',6'-dichloro-phenyl)-amino]-2-imidazoline in 75 ml of absolute tetrahydrofuran at 10°–20° C. The resulting mixture was stirred at room temperature for 2 hours, and then a mixture of 2.24 ml (0.03 mol) of propargyl bromide and 15 ml of absolute tetrahydrofuran was added dropwise at room temperature, while stirring. The mixture was allowed to react for 2 hours at room temperature and was subsequently refluxed for 2 hours. Thereafter, the reaction mixture was evaporated in vacuo, and the residue was dissolved in dilute hydrochloric acid. The acidic aqueous solution was extracted several times with ether (the ethereal extracts were discarded) and then adjusted stepwise to gradually increasing pH-values with 2 N sodium hydroxide; after each pH-adjustment the solution was extracted with ether. The thin-layer chromatographically uniform extracts were combined, dried over anhydrous calcium sulfate, and evaporated to dryness, yielding as the pure, white residue 4.2 gm (52.2% of theory) of the compound of the formula

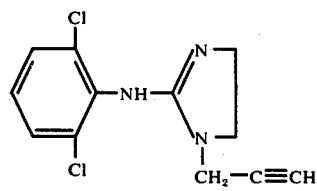

having a melting point of 98°–100° C. The product was soluble in most conventional organic solvents, such as ethanol or ether.

EXAMPLE 20

Using a procedure analogous to that described in Example 19, 36.1% of theory of 1-propargyl-2-[N-(2'-methyl-5'-fluoro-phenyl)-amino]-2-imidazoline, m.p. 84°–85° C, was obtained from 2-[N-(2'-methyl-5'-fluoro-phenyl)-amino]-2-imidazoline, sodium hydride and propargyl bromide.

EXAMPLE 21

Using a procedure analogous to that described in Example 19, 8.4% of theory of 1-propargyl-2-anilino-2-imidazoline, an oil, was obtained from 2-anilino-2-imidazoline, sodium hydride and propargyl bromide.

EXAMPLE 22

Using a procedure analogous to that described in Example 19, 55.2% of theory of 1-propargyl-2-[N-(2',4'-dichloro-phenyl)-amino-]-2-imidazoline, m.p. 64.5°–66° C, was obtained from 2-[N-(2',4'-dichloro-phenyl)-amino]-2-imidazoline, sodium hydride and propargyl bromide.

EXAMPLE 23

Using a procedure analogous to that described in Example 19, 48.5% of theory of 1-propargyl-2-[N-(2'-chloro-6'-methyl-phenyl)-amino]-2-imidazoline, an oil, was obtained from 2-[N-(2'-chloro-6'-methyl-phenyl)-amino]-2-imidazoline, sodium hydride and propargyl bromide.

EXAMPLE 24

Using a procedure analogous to that described in Example 19, 45.2% of theory of 1-propargyl-2-[N-(2'-chloro-4'-methyl-phenyl)-amino]-2-imidazoline, an oil, was obtained from 2-[N-(2'-chloro-4'-methyl-phenyl)-amino]-2-imidazoline, sodium hydride and propargyl bromide.

The compounds of the present invention, that is, those embraced by formula I and their non-toxic, pharmacologically acceptable acid addition salts, have useful pharmacodynamic properties. More particularly, they exhibit analgesic and hypotensive activities in warm-blooded animals, such as mice, and are therefore useful for alleviating pain and treating hypertonia.

In the hot-plate test [Woolfe et al., J. Pharmacol. 80, 300 (1944)] on mice, for instance, the end product of Example 2 exhibited an analgesic activity which was about 100 times stronger than that of morphine. Moreover, that particular compound of the present invention produces virtually no effect upon the circulatory system at dosages of up to 3 mgm/kg; therefore, the ratio of analgesic to hypotensive activity in this particular compound is more than 300 times more favorable with respect to the analgesic activity vector than in the case of clonidin.

For pharmaceutical purposes the compounds of the present invention are administered to warm-blooded animals enterally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0016 to 1.3 mgm/kg body weight, preferably 0.0083 to 0.5 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 25

Tablets

The tablet composition is compounded from the following ingredients:

| | | |
|---|---|---|
| 2-[N-Propargyl-N-(2',6'-dichloro-phenyl)-amino]-2-imidazoline | 30 parts | |
| Corn starch | 160 " | |
| Secondary calcium phosphate | 250 " | |
| Magnesium stearate | 5 " | |
| Total | 445 parts | |

Preparation

The individual ingredients are intimately admixed with each other, the mixture is granulated in conventional manner, and the granulate is compressed into 445 mgm-tablets. Each tablet contains 30mgm of the imidazoline compound and is an oral dosage unit composition with effective analgesic action.

EXAMPLE 26

Gelatin capsules

The capsule filler composition is compounded from the following ingredients:

| | | |
|---|---|---|
| 1-Propargyl-2-[N-2',6'-dichloro-phenyl)-amino]-2-imidazoline | 25 parts | |
| Corn starch | 175 " | |
| Total | 200 parts | |

Preparation

The ingredients are intimately admixed with each other, and 200 mgm-portions of the mixture are filled into gelatin capsules of suitable size. Each capsule contains 25 mgm of the imidazoline compound and is an oral dosage unit composition with effective analgesic action.

EXAMPLE 27

Hypodermic solution

The solution is compounded from the following ingredients:

| | | |
|---|---|---|
| 2-[N-Propargyl-N-(2',3'-dichloro-phenyl)-amino]-2-imidazoline | | 1.5 parts |
| Sodium salt of EDTA | | 0.2 " |
| Distilled water | q.s.ad | 100.0 " |

Preparation

The imidazoline compound and the EDTA salt are dissolved in a sufficient amount of distilled water, the solution is diluted with additional distilled water to the indicated amount, the resulting solution is filtered until free from suspended particles, and the filtrate is filled into 2 ml-ampules under aseptic conditions. The filled ampules are then sterilized and sealed. Each ampule contains 20 mgm of the imidazoline compound, and its contents are an injectable dosage unit composition with effective analgesic action.

Analogous results are obtained when any one of the other 2-phenylamino-2-imidazolines embraced by formula I or a non-toxic, pharmacologically acceptable acid addition salt thereof is substituted for the particular 2-phenylaminoimidazoline in Examples 25 through 27. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

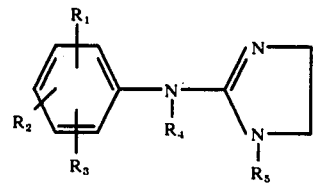

wherein
$R_1$, $R_2$ and $R_3$ are each hydrogen, fluorine, chlorine, bromine, methyl, ethyl or methoxy or trifluoromethyl when sterically possible, and one of $R_4$ and $R_5$ is propargyl and the other is hydrogen, or a non-toxic, pharmacologically acceptable acid addition salt thereof.

2. A compound of claim 1,
where
$R_1$, $R_2$ and $R_3$ are each hydrogen, fluorine, chlorine, bromine, methyl, ethyl, methoxy or trifluoromethyl,
$R_4$ is propargyl, and
$R_5$ is hydrogen.

3. A compound of claim 2, which is 2-[N-propargyl-N-(2',6'-dichloro-phenyl)-amino]-2-imidazoline or a non-toxic, pharmacologically acceptable acid addition salt thereof.

4. A compound of claim 2, which is 2-[N-propargyl-N-(2',3'-dichloro-phenyl)-amino]-2-imidazoline or a non-toxic, pharmacologically acceptable acid addition salt thereof.

5. A compound of claim 1,
where
$R_1$, $R_2$ and $R_3$ are each hydrogen, fluorine, chlorine, bromine, methyl, ethyl, methoxy, or trifluoromethyl,
$R_4$ is hydrogen, and
$R_5$ is propargyl.

6. A compound of claim 5, which is 1-propargyl-2-[N-(2',6'-dichloro-phenyl)-amino]-2-imidazoline or a non-toxic, pharmacologically acceptable acid addition salt thereof.

7. An analgesic or hypotensive pharmaceutical dosage unit composition consisting essentially of an inert pharmaceutical carrier and an effective analgesic or hypotensive amount of a compound of claim 1.

8. The method of alleviating pain or treating hypertonia in a warm-blooded animal, which comprises enterally or parenterally administering to said aimal an effective analgesic or hypotensive amount of a compound of claim 1.

* * * * *